United States Patent
Schmitt et al.

(10) Patent No.: US 9,649,277 B2
(45) Date of Patent: May 16, 2017

(54) MULTICOMPARTMENTALIZED MATERIAL FOR THE THERMOSTIMULATED DELIVERY OF SUBSTANCES OF INTEREST, PREPARATION PROCESS AND APPLICATIONS

(71) Applicant: CENTRE NATIONAL DE LA RECHERCHE SCIENTIFIQUE, Paris (FR)

(72) Inventors: Veronique Schmitt, Talence (FR); Maxime Nollet, Bordeaux (FR); Martin Depardieu, Orleans (FR); Renal Backov, Bordeaux-Caudera (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/409,177

(22) PCT Filed: Jun. 20, 2013

(86) PCT No.: PCT/FR2013/051438
§ 371 (c)(1),
(2) Date: Dec. 18, 2014

(87) PCT Pub. No.: WO2013/190240
PCT Pub. Date: Dec. 27, 2013

(65) Prior Publication Data
US 2015/0190342 A1     Jul. 9, 2015

(30) Foreign Application Priority Data
Jun. 21, 2012 (FR) ................................. 12 55844

(51) Int. Cl.
| A61K 9/14 | (2006.01) |
|---|---|
| A61K 8/02 | (2006.01) |
| A61K 8/11 | (2006.01) |
| B01J 13/18 | (2006.01) |
| B01J 13/22 | (2006.01) |
| C09B 67/02 | (2006.01) |
| A61K 9/00 | (2006.01) |
| A61K 9/50 | (2006.01) |
| A61K 8/25 | (2006.01) |
| A61K 8/31 | (2006.01) |
| A61K 8/36 | (2006.01) |
| A61K 8/37 | (2006.01) |
| A61Q 15/00 | (2006.01) |
| A61Q 19/00 | (2006.01) |
| A61K 8/92 | (2006.01) |
| A23P 10/35 | (2016.01) |
| A23P 20/00 | (2016.01) |

(52) U.S. Cl.
CPC .............. *A61K 9/143* (2013.01); *A23P 10/35* (2016.08); *A23P 20/19* (2016.08); *A61K 8/025* (2013.01); *A61K 8/0241* (2013.01); *A61K 8/11* (2013.01); *A61K 8/25* (2013.01); *A61K 8/31* (2013.01); *A61K 8/361* (2013.01); *A61K 8/375* (2013.01); *A61K 8/922* (2013.01); *A61K 9/0004* (2013.01); *A61K 9/501* (2013.01); *A61Q 15/00* (2013.01); *A61Q 19/00* (2013.01); *B01J 13/18* (2013.01); *B01J 13/22* (2013.01); *C09B 67/0097* (2013.01); *A23V 2002/00* (2013.01); *A61K 2800/412* (2013.01); *A61K 2800/56* (2013.01)

(58) Field of Classification Search
CPC ..... A23L 1/0032; A23L 1/0053; A61K 9/143; A61K 8/025
See application file for complete search history.

(56) References Cited

U.S. PATENT DOCUMENTS

| 2011/0195099 A1 | 8/2011 | Nolte et al. | |
|---|---|---|---|
| 2012/0128747 A1* | 5/2012 | Veronique | ................ B01J 13/18 424/401 |
| 2015/0151267 A1* | 6/2015 | Schmitt | .................... A61K 8/11 424/401 |

FOREIGN PATENT DOCUMENTS

CN            101824307          9/2010

OTHER PUBLICATIONS

Search Report Dated 2013.

* cited by examiner

*Primary Examiner* — Gina Justice
(74) *Attorney, Agent, or Firm* — Sofer & Haroun, LLP

(57) ABSTRACT

The present invention relates to a material in the form of solid particles with a diameter varying from 1 μm to 1 cm which are composed of a continuous shell $E_{Ext}$ comprising at least one silicon oxide, said shell $E_{Ext}$ imprisoning at least one fatty phase, said material being characterized in that said fatty phase is solid at the storage temperature of said material and predominantly comprises a crystallizable oil having a melting point ($T_M$) of less than 100° C. and in that said fatty phase includes at least one lipophilic substance of interest $S_L$ and at least one inclusion comprising a continuous shell $E_{Int}$ comprising at least one silicon oxide, said shell $E_{Int}$ imprisoning an aqueous phase comprising at least one hydrophilic substance of interest $S_H$.

The invention also relates to a process for the preparation of said material, to its use for the thermostimulated delivery of active substances, and also to the compositions including it.

22 Claims, 3 Drawing Sheets

MULTICOMPARTMENTALIZED MATERIAL FOR THE THERMOSTIMULATED DELIVERY OF SUBSTANCES OF INTEREST, PREPARATION PROCESS AND APPLICATIONS

RELATED APPLICATIONS

This application is a National Phase Application of PCT/FR2013/051438, filed on Jun. 20, 2013, which in turn claims the benefit of priority from French Patent Application No. 12 55844 filed on Jun. 21, 2012, the entirety of which are incorporated herein by reference.

BACKGROUND

Field of the Invention

The present invention relates to a material composed of a silica shell including a fatty phase in which are dispersed silica capsules including an aqueous phase, to its process of preparation, to its use for the thermostimulated delivery of active substances and to the compositions including such a material.

Description of Related Art

It may be of use to encapsulate molecules of interest, such as medicaments, dyes, pigments, reactants, fragrances, pesticides, and the like, in order to protect them from external attacks, in particular from oxidation, in order to convey them to a site of administration where they can be delivered or else in order to store them before use under conditions where they will be released from their capsule under the influence of an external stimulus. One of the first applications of microencapsulation was the development of a carbonless copy paper commercialized at the end of the 1960s, in which microcapsules imprisoning an ink were present on the back of a paper sheet so as to release the ink by rupture of the capsules under the pressure exerted by the tip of a pen during writing. At the present time, encapsulation is growing in various industrial sectors, such as pharmaceutical, cosmetics, food, textile and agricultural industries. Capsules and microcapsules are becoming increasingly sophisticated, in particular in the pharmaceutical field, where they make it possible to bring about the controlled and/or targeted delivery of active principles.

Various types and morphologies of capsules and microcapsules have already been provided, such as, for example, protein capsules, cyclodextrins, liposomes, concentrated lamellar vesicles, double emulsions, colloidosomes, microcapsules comprising silica shells, nanocapsules of silica and of heat-sensitive polymers, such as poly(N-isopropylacrylamide) (PNIPAM), heat-sensitive hydrogel microspheres. PNIPAM-Polylactide microspheres, and the like. Numerous methods which make it possible to prepare these various types of capsules and microcapsules have also been developed and perfected in recent years, such as, for example and non-exhaustively, the precipitation of polymers by phase separation, layer-by-layer electrolyte deposition, polymerization by interfacial polycondensation, and the like.

The disadvantage of the techniques already known is that the release of the molecules of interest from the capsules and microcapsules provided in the prior art is generally slow and gradual, that is to say prolonged over time.

Provision was then made to overcome this problem by providing materials composed of a silica shell including a wax core comprising one or more substances of interest, these materials being prepared by mineralization of a Pickering emulsion, that is to say of an emulsion of oil-in-water type in which the dispersion of the oil droplets in the water is stabilized by colloidal nanoparticles adsorbed at the water/oil interface (see, for example, Patent Application FR-A-2 948 581). By using a crystallizable oil to prepare these materials, that is to say an oil having a fairly low melting point ($T_M$) (for example, 37° C.), it is possible to prepare materials in which the encapsulated phase is solid under the storage conditions (for example, at ambient temperature) but becomes liquid under the conditions of use of the material (for example, at a temperature greater than 37° C. in the case of an ingestible or injectable medicament), thus bringing about the rupture of the capsule by melting and thermal expansion of the encapsulated phase and the concomitant and rapid release of the active substance or substances present in the encapsulated phase. These materials make it possible to encapsulate both lipophilic substances of interest (in the dissolved form) and hydrophilic substances of interest (in the dispersed form). However, when the encapsulated phase of these materials includes several substances of different chemical nature, these are in contact with one another, which does not make it possible, within one and the same material, to encapsulate substances which may exhibit a chemical and/or physical incompatibility. Furthermore, these materials do not make it possible to simultaneously comprise hydrophilic and lipophilic substances both in the dissolved form since only the lipophilic substances can be present in the dissolved form in the fatty phase encapsulated by the silica shell, whereas the hydrophilic substances are in the dispersed form therein.

There thus currently does not exist a compartmentalized system which makes it possible to encapsulate in the dissolved form, within one and the same material, at least two substances of interest which may furthermore possibly be incompatible with one another, said substances being lipophilic or hydrophilic, and which allows rapid and complete release of these substances of interest under the effect of an external stimulus under mild conditions.

OBJECTS AND SUMMARY

The aim of the present invention is thus to provide a material which makes it possible to encapsulate several molecules of interest in compartmentalized fashion and which also makes possible their rapid and complete release under the influence of an external stimulus and in particular of an increase in the temperature.

A subject-matter of the present invention is a material in the form of solid particles with a diameter varying from 1 μm to 1 cm which are composed of a continuous shell $E_{Ext}$ comprising at least one silicon oxide, said shell $E_{Ext}$ imprisoning at least one fatty phase, said material being characterized in that said fatty phase is solid at the storage temperature of said material and comprises from 50% to 99.9% by weight, with respect to the weight of said fatty phase, of a crystallizable oil having a melting point ($T_M$) of less than 100° C. and in that said fatty phase includes at least one lipophilic substance of interest $S_L$ and at least one inclusion comprising a continuous shell $E_{Int}$ comprising at least one silicon oxide, said shell $E_{Int}$ imprisoning an aqueous phase comprising at least one hydrophilic substance of interest $S_H$.

According to the present invention, the term "storage temperature of said material" is understood to mean the temperature at which the material in accordance with the present invention is stored before it is used. This temperature is always less than the melting point of the crystallizable oil present in the fatty phase. Generally, the storage temperature corresponds to a temperature of less than or equal to ambient temperature (approximately 20° C.).

The material in accordance with the present invention exhibits the following distinguishing feature: when the material is subjected to a temperature greater than the melting point of the crystallizable oil, a thermal expansion of the fatty phase is observed, bringing about the rupture of the silica shell $E_{Ext}$, and also the rupture of the shell or shells $E_{Int}$, and the rapid and complete release of the molten fatty phase (that is to say, in the liquid state) comprising the substance or substances of interest $S_L$, and also the release of the aqueous phase present in the inclusions and comprising the substance or substances $S_H$. This result is entirely surprising in so far as the silicon oxide participating in the composition of the shell is known to be a thermal insulator. Furthermore, it was not at all obvious that the thermal expansion of the fatty phase would make it possible to bring about both the rupture of the shell $E_{Ext}$ and the rupture of the shell or shells $E_{Int}$.

In the context of this account, the term "crystallizable oil" is understood to mean fatty substances or mixtures of fatty substances, of natural (animal or vegetable) or synthetic origin, the melting point of which is greater than 15° C., the melting point of which preferably varies from 20 to 100° C. approximately and in particular from 20 to 50° C. approximately. All the melting points mentioned in the description of the present patent application refer to melting points determined by differential scanning calorimetry (DSC) at atmospheric pressure.

The crystallizable oil forms a predominant part of the fatty phase and can even, apart from the substance or substances of interest $S_L$ and the inclusions, be the only constituent of the fatty phase. The crystallizable oil preferably represents from 75% to 99.9% by weight approximately, with respect to the weight of the fatty phase.

The choice of the crystallizable oil naturally depends on the application envisaged for the material and thus on the temperature at which it is desired to observe the thermal expansion of the fatty phase and consequently the rupture of the silica shells $E_{Ext}$ and $E_{Int}$. Mention may in particular be made, among the crystallizable oils which can be used according to the invention, of paraffin oils, such as the paraffin oils having a melting point between 42 and 44° C. or between 46 and 48° C. [RN-8002-74-2] sold by Merck, triglycerides, fatty acids, rosins, waxes (long alkanes), such as icosane and octadecane, hydrogenated vegetable oils and their mixtures, and synthetic bitumens. These oils can be used alone or as mixtures.

The material in accordance with the present invention is preferably provided in the form of a powder of spherical or substantially spherical particles.

The diameter of the particles preferably varies from 5 μm to 500 μm approximately and more preferably still from 10 to 200 μm.

The silica shell $E_{Ext}$ must have a thickness sufficient to have a mechanical strength which makes possible the encapsulation of the fatty phase. However, the silica shells $E_{Ext}$ and $E_{Int}$ must also exhibit a thickness which allows them to burst during a rise in the temperature to a temperature greater than the melting point of the fatty phase. The thickness of the silica shell $E_{Ext}$ generally varies from 0.1 to 2 μm approximately and preferably from 0.2 to 2 μm approximately.

The thickness of the silica shell or shells $E_{Int}$ generally varies from 0.1 to 1 μm approximately and preferably from 0.2 to 0.8 μm approximately.

In addition to the silicon oxide, the shells $E_{Ext}$ and/or $E_{Int}$ can additionally comprise one or more metal oxides of formula $MeO_2$ in which Me is a metal chosen from Zr, Ti, Th, Nb, Ta, V, W and Al. In this case, the shells $E_{Ext}$ and $E_{Int}$ are composed of a mixed matrix of $SiO_2$-$MeO_2$ type in which the content of $MeO_2$ remains minor with respect to the content of silicon oxide; preferably, the content of $MeO_2$ represents from 1% to 40% by weight, more particularly from 5% to 30% by weight, with respect to the total weight of the shell.

Mention may in particular be made, among the substances of interest which can be incorporated in the fatty phase and in the aqueous phase of the inclusion or inclusions of the material in accordance with the present invention, of medicaments (active principles), active principles which can be used in cosmetics, chemical reactants, dyes, pigments, inks, and the like. Of course, these substances are incorporated in the fatty phase when they are lipophilic and in the aqueous phase of the inclusion or inclusions when they are hydrophilic, a person skilled in the art knowing how to distinguish the lipophilic or hydrophilic nature of a given substance as a function of its HLB ("Hydrophilic-Lipophilic Balance") value.

Mention may be made, as examples of medicaments, of bactericides, such as antiseptics and antibiotics, anti-inflammatories, analgesics, local laxatives, hormones, proteins, and the like.

Mention may in particular be made, as examples of cosmetic active principles, of vitamins, sunscreens, antioxidants, such as agents for combating free radicals, for example superoxide dismutase, fragrances, odour absorbers, deodorant agents, antiperspirant agents, dyes, pigments, emollients, moisturizing agents, and the like.

Mention may in particular be made, as examples of chemical reactants, of coloured reactants, coloured indicators, such as pH indicators, catalysts, polymerization initiators, monomers, complexing agents, and the like.

The substance or substances of interest $S_L$ generally represent from 0.001% to 50% by weight approximately and preferably from 0.01% to 25% by weight approximately of the total weight of the fatty phase.

The substance or substances of interest $S_H$ generally represent from 0.001% to 50% by weight approximately and preferably from 0.01% to 25% by weight approximately of the total weight of the aqueous phase present in the inclusion or inclusions present within the fatty phase.

The fatty phase and/or the aqueous phase of the inclusion or inclusions can, in addition, include one or more additives conventionally used in emulsions and among which may in particular be mentioned, by way of example, agents for protecting or preserving the substance of interest, such as antioxidants, UV inhibitors, and the like.

Another subject-matter of the invention is a process for the preparation of the material as defined above. This process is characterized in that it comprises the following stages, consisting:

1) in a first stage, in bringing a fatty phase comprising from 50% to 99.9% by weight, with respect to the weight of said fatty phase, of a solid crystallizable oil (CO) having a melting point $T_M$ of less than 100° C. to a temperature $T_{CO}$ such that $T_{CO}$ is greater than $T_M$, in order to obtain a crystallizable oil in the liquid state;

2) in a second stage, in incorporating, in the fatty phase in the liquid state, at least one lipophilic substance of interest ($S_L$) and solid colloidal particles P1;

3) in a third stage, in bringing said fatty phase in the liquid state into contact with a first aqueous phase (AP1) brought beforehand to a temperature $T_{AP1}$ such that $T_{AP1}$ is greater than $T_M$, said aqueous phase additionally including at least one hydrophilic substance of interest ($S_H$);

4) in a fourth stage, in subjecting the liquid mixture resulting from the third stage to mechanical stirring in order to obtain a water-in-oil (W/O) emulsion formed of droplets of aqueous phase dispersed in the continuous fatty phase in the liquid state and in which the solid colloidal particles P1 are present at the interface formed between the continuous fatty phase and the dispersed droplets of aqueous phase AP1;

5) in a fifth stage, in adding the W/O emulsion obtained above in the preceding stage to a second aqueous phase (AP2) brought beforehand to a temperature $T_{AP2}$ such that $T_{AP2}$ is greater than $T_M$ and additionally including solid colloidal particles P2, said W/O emulsion representing at most 20% by weight with respect to the weight of the second aqueous phase;

6) in a sixth stage, in subjecting the liquid mixture resulting from the fifth stage to mechanical stirring in order to obtain a water-in-oil-in-water (W/O/W) double emulsion formed of a continuous aqueous phase (AP2) including droplets of fatty phase in the liquid state, each of said droplets of fatty phase in the liquid state including at least one droplet of aqueous phase AP1, in which double emulsion the solid colloidal particles P2 are present at the interface formed between the continuous aqueous phase AP2 and the dispersed droplets of fatty phase in the liquid state;

7) in a seventh stage, in bringing said W/O/W double emulsion to a temperature $T_{W/O/W}$ such that $T_{W/O/W}$ is less than $T_M$ in order to bring about the solidification of the fatty phase and to obtain a W/O/W double emulsion formed of globules of fatty phase in the solid state, each of said globules including at least one droplet of aqueous phase AP1, said globules being dispersed in the aqueous phase AP2;

8) in an eighth stage, in adding, to the aqueous phase AP2 of the double emulsion and with mechanical stirring, at least one silicon oxide precursor and a sufficient amount of at least one acid to bring the aqueous phases AP1 and AP2 to a pH of less than or equal to 4;

9) in a ninth stage, in leaving the W/O/W double emulsion standing, in order to allow the silicon oxide precursor to hydrolyse and to condense in the form of a silicon oxide shell around said droplets of aqueous phase AP (mineralization of the emulsion) and to thus obtain the expected material;

10) in a tenth stage, in separating said material from the aqueous phase AP2.

The solid colloidal particles P1 added to the fatty phase during the second stage and the particles P2 present in the aqueous phase AP2 during the fifth stage can be inorganic or organic. Preferably, they are inorganic particles chosen from the group of metal oxides, hydroxides and sulphates. Mention may very particularly be made, among such oxides, of oxides of silicon, titanium, zirconium and iron, and also their salts, such as silicates (for example clays). Finally, mention may be made of colloidal carbon particles. Mention may in particular be made, among solid organic colloidal particles, of polymeric particles, for example latex particles.

In order to be colloidal, the solid particles P1 and P2 generally exhibit a size of less than a few micrometers. Thus, the particles generally exhibit a mean size of between 5 and 5000 nm and preferably between 5 and 500 nm.

According to a particularly preferred embodiment of the invention, the solid colloidal particles P1 and P2 are identical in chemical nature and are chosen from silicon oxide nanoparticles. Mention may in particular be made, by way of example, of the products sold under the Aerosil® trade name by Evonik Degussa. In this case, the particles P1 and P2 can be identical or different in diameter. Use may for example be made, as particles P1, of silicon oxide particles having a mean diameter of approximately 12 nm and, as particles P2, of silicon oxide particles having a mean diameter of approximately 16 nm.

The amount of solid colloidal particles P1 generally varies from 0.01% to 10% by weight and in particular from 0.1% to 7% by weight, with respect to the total weight of the aqueous phase AP1.

Advantageously, the amount of solid colloidal particles P1 present in the fatty phase varies as a function of the mean size by volume of the droplets of aqueous phase AP1 which are desired in the emulsion, the mean diameter of which varies from 0.1 μm to 100 μm, preferably from 1 to 50 μm and more preferably still from 5 to 20 μm approximately.

The amount of solid colloidal particles P2 generally varies from 0.01% to 5% by weight and in particular from 0.5% to 2% by weight, with respect to the total weight of the W/O emulsion.

Advantageously, the amount of solid colloidal particles P2 present in the aqueous phase AP2 varies as a function of the mean size by volume of the dispersed droplets of fatty phase which are desired in the emulsion, the mean diameter of which varies from 15 to 100 μm, preferably from 30 to 80 μm and more preferably still from 40 to 70 μm approximately.

Furthermore, the solid colloidal particles (P1 and P2) generally exhibit a hydrophilic and charged surface which does not promote their adsorption at the surface of the dispersed droplets of the aqueous phase AP1 or at the surface of the droplets of fatty phase dispersed in the aqueous phase AP2.

Thus, and according to a preferred embodiment of the invention, the solid colloidal particles P1 and P2 are functionalized at the surface in order to promote their adsorption at the interface formed between the continuous fatty phase and the aqueous phase AP1 during stage 4) or between the aqueous phase AP2 and the dispersed droplets of fatty phase during stage 6).

The solid colloidal particles P1 and P2 can thus be functionalized by compounds bonded to their surface via covalent bonds. This can be carried out by prior treatment of the particles, in particular by chemical grafting of a compound comprising hydrophobic groups, such as a trialkoxysilane of formula R—Si—(OR')$_3$, in which R is a linear or branched $C_1$ to $C_{12}$ alkyl, in particular from $C_2$ to $C_{10}$, very particularly n-octyl, optionally carrying an amino group, and R', which is identical to or different from R, is a linear or branched $C_1$ to $C_{12}$ alkyl group, in particular from $C_1$ to $C_6$, and very particularly ethyl.

The solid colloidal particles P1 and P2 can also be functionalized by adsorption of surfactant molecules at their surface which makes it possible to confer on them a degree of hydrophobicity, the hydrophilic end of the surfactant being adsorbed on the surface of the particles. The surfactants which can be used to functionalize the particles P1 and P2 are preferably cationic or anionic surfactants.

Preference is given, among these surfactants, in particular to sodium alkyl sulphates, such as, in particular, sodium dodecyl sulphate (SDS), and alkyltrimethylammonium bromides.

The surfactant is preferably chosen from surfactants having an opposite charge to that of the surface of the solid colloidal particles P1 and P2. This choice makes it possible to promote the adsorption of the surfactant at the surface of the particles.

Mention may in particular be made, as example of particles functionalized by a surfactant, of silica nanoparticles, the surface of which is functionalized by a quaternary ammonium, such as those sold under the name Aerosil® A380 by Evonik Degussa, with a diameter of 7 nm, the surface of which is functionalized by cetyltrimethylammonium bromide (CTAB), silica nanoparticles with a diameter of 12 nm, sold under the name Aerosil® AR 816, and silica nanoparticles with a diameter of 16 nm, sold under the name Aerosil® AR 972 by Evonik Degussa.

The functionalization of the solid colloidal particles P1 and P2 by a surfactant can also be carried out in situ, that is to say during their introduction into the fatty phase and respectively into the aqueous phase AP2 of the emulsion. In this case, the fatty phase and the aqueous phase AP2 of the emulsion additionally include said surfactant in an amount preferably below the critical micelle concentration (CMC), the surfactant then being adsorbed at the surface of the particles when the latter are in the aqueous phase of the emulsion. Preferably, the amount of surfactant varies from $1/200^{th}$ to $1/3$ of the CMC.

The aqueous phases AP1 and AP2 mainly comprise water and optionally an alcohol, such as methanol, ethanol, isopropanol or butanol, preferably ethanol.

The mechanical stirring operations carried out during the fourth and sixth stages can in particular be carried out in a device intended to emulsify, such as, for example, in devices sold under the Ultra-Turrax® or Rayneri® trade names.

The size distribution of the droplets of the aqueous phase AP1 in the W/O emulsion is generally narrow (U<40%).

During the ninth stage (mineralization of the emulsion), the addition of at least one silicon oxide precursor at acid pH brings about the condensation of said precursor at the interface formed between the globules of fatty phase in the solid state and the aqueous phase AP2 and also at the interface between the droplets of aqueous phase AP1 and the fatty phase. There is thus simultaneous formation of a silica shell around each of the droplets of aqueous phase AP1 present in each of the droplets of fatty phase, and also of a silica shell around each of the droplets of fatty phase.

The silicon oxide precursors can be chosen from silicon alkoxides and in particular from tetramethoxyorthosilane (TMOS), tetraethoxyorthosilane (TEOS), dimethyldiethoxysilane (DMDES), (3-mercaptopropyl)trimethoxysilane, (3-aminopropyl)triethoxysilane, N-(3-trimethoxysilylpropyl)pyrrole, 3-(2,4-dinitrophenylamino)propyltriethoxysilane, N-(2-aminoethyl)-3-aminopropyltrimethoxysilane, phenyltriethoxysilane, methyltriethoxysilane and their mixtures. Among these precursors, TEOS is particularly preferred. These precursors can be completely or partially replaced by silicate sols.

The thickness of the shell formed around each droplet of aqueous phase AP1 and also around each droplet of fatty phase depends on the amount of silicon oxide precursors used during the eighth stage and on the diameter of the dispersed droplets of the fatty phase and also on the diameter of the droplets of aqueous phase AP1 dispersed in the fatty phase. This amount is expressed with respect to the total surface area in m$^2$ of the globules of the dispersed phase of the emulsion and of the dispersed droplets of aqueous phase AP1.

According to a preferred embodiment of the invention, the amount of silicon oxide precursor varies from 0.005 to 4 M/m$^2$ and more preferably still from 0.01 to 2.2 M per m$^2$ of total surface area of the globules of the dispersed phase and of the droplets of aqueous phase AP1 of the emulsion.

In order to achieve greater shell thicknesses, stages 8 to 10 can be carried out several times until the desired thickness is obtained.

When the silica shells of the material in accordance with the invention comprise a metal oxide in addition to the silicon oxide, at least one precursor of a metal oxide of formula MeO$_2$ is then also added to the aqueous phases AP1 and AP2 of the emulsion, said precursor being chosen from the alkoxides, chlorides or nitrates of the metals chosen from Zr, Ti, Th, Nb, Ta, V, W and Al.

When they are used, the amount of these precursors of metal oxide of formula MeO$_2$ varies from 0.001 M to 1 M and preferably from 0.01 to 0.6 M per m$^2$ of total surface area of the globules of the dispersed phase and of the droplets of aqueous phase AP1 of the emulsion.

The pH of the aqueous phases AP1 and AP2 during the eighth stage preferably varies from 0.01 to 4 and more preferably still from 0.1 to 2.1.

The acid used to adjust the pH of the aqueous phases AP1 and AP2 can be chosen from inorganic and organic acids, among which may in particular be mentioned hydrochloric acid, acetic acid, nitric acid and sulphuric acid.

During the tenth stage, the material in accordance with the invention can be separated from the aqueous phase and recovered by any conventional separation technique known to a person skilled in the art, such as filtration, centrifuging and the use of sieves. It is subsequently preferably washed, for example with water, and then dried, for example by freeze drying, to give a powder.

The material thus obtained is stable on storage for several months provided that the storage temperature is less than the melting point $T_M$ of the fatty phase imprisoned in the silica shell.

The material in accordance with the invention can be used in the powder form or in the form of a dispersion in a solvent in order to deliver the lipophilic substance or substances of interest present in the solid fatty phase imprisoned in the silica-based shell and also the hydrophilic substance or substances of interest present in the inclusions of aqueous phase AP1, said aqueous phase AP1 being itself imprisoned and separated from the fatty phase by a silica shell.

Another subject-matter of the invention is thus the use of a material in accordance with the invention and as described above for the thermostimulated and simultaneous delivery of at least one lipophilic substance of interest and of at least one hydrophilic substance of interest.

The delivery of the lipophilic and hydrophilic substances of interest is obtained by thermal expansion of the fatty phase, bringing about rupture of the shell surrounding the fatty phase as well as rupture of each of the silica shells surrounding each of the droplets of aqueous phase AP1 dispersed in the fatty phase, under the effect of a rise in the temperature of the material to a delivery temperature $T_D$ such that $T_D > T_M$.

By way of example and when the substances of interest are lipophilic and hydrophilic active principles having a medicinal action or food supplement active ingredients, such as, for example, lipophilic and hydrophilic vitamins, the crystallizable oil present in the fatty phase is preferably chosen from crystallizable oils having a melting point of less than 37° C. Thus, when said material is incorporated in a pharmaceutical composition and when this composition is administered to a patient, for example orally, the composition ingested will be at body temperature, generally 37° C. or more, which will result in the melting of the fatty phase and in its expansion in volume and thus rupture of the silica shells and the delivery of the active principles or of the active ingredients.

According to another example, the lipophilic and hydrophilic substances of interest are cosmetic active principles and the material is one of the components of a cosmetic composition for topical application, such as a powder, a cream or a gel. The heating of the fatty phase of the material to a temperature greater than $T_M$ can in this case be brought about by local rubbing during the spreading of the cosmetic composition, which causes local heating bringing about rupture of the shells and the local release of the substances of interest. If the cosmetic composition is provided in the form of a powder, its application by spreading can be accompanied by a change in texture (transformation of the powder into a composition having a greasy feel due to rupture of the shell).

Mention may in particular be made, as other examples of the use of the material in accordance with the invention, of:
 the use for the simultaneous delivery of lipophilic and hydrophilic initiators of a polymerization reaction brought about by a rise in the temperature; in this case, the material in accordance with the invention can, for example, be used for the manufacture of solid foams in the field of insulating materials.

Another subject-matter of the invention is the use of the material as described above as ingredient for the preparation of pharmaceutical, cosmetic or food products and also the pharmaceutical, cosmetic or food products including, as ingredient, at least one material in accordance with the invention.

These compositions can include conventional pharmaceutical, cosmetic or food vehicles well known to a person skilled in the art and also one or more surfactants intended to promote the release of the liquid fatty phase and of the encapsulated aqueous phase during rupture of the various silica shells.

DETAILED DESCRIPTION

The present invention is illustrated by the following implementational examples, to which, however, it is not limited.

EXAMPLES

The starting materials used in the examples which follow are listed below:
 Icosane, 99% pure (melting point=37° C.), sold by Sigma-Aldrich;
 Tetraethoxyorthosilane, more than 99% pure (TEOS);
 Rhodamine B: Sigma-Aldrich;
 Cetyltrimethylammonium bromide (CTAB): ChemPur;
 Silica nanoparticles with a diameter of 12 nm, sold under the name Aerosil® AR 816, and silica nanoparticles with a diameter of 16 nm, sold under the name Aerosil® AR 972: Evonik Degussa.

These starting materials were used as received from the manufacturers, without additional purification.

The critical micelle concentration (CMC) of the CTAB in pure water at ambient temperature is 0.92 mM.

The materials obtained were characterized using an inverted optical microscope sold under the trade name Axiovert® X100 by Zeiss and equipped with a heating stage from Mettler which makes it possible to control the temperature and also the heating and cooling rates.

The size distribution of the emulsions was studied using a particle sizer sold under the trade name Mastersizer Hydro MS2000 by Malvern Instrument. The particle size measurements were carried out at 25° C. in pure water. The intensity of the scattering as a function of the angle which was collected was converted using the Mie-Lorenz theory. The distribution in the size of the particles was expressed by their weighted mean diameter (D) and their polydispersity (P) by applying the following equations (1) and (2):

$$D = \frac{\sum_i N_i D_i^3}{\sum_i N_i D_i^2} \tag{1}$$

and $$P = \frac{1}{\overline{D}} \frac{\sum_i N_i D_i^3 |\overline{D} - D_i|}{\sum_i N_i D_i^3} \tag{2}$$

in which:
 $D_i$ is the diameter of the particles,
 $N_i$ is the total number of droplets with the diameter $D_i$,
 $\overline{D}$ is the median diameter, that is to say the theoretical opening of the sieve such that 50% of the particles, by weight, have a greater diameter and 50% have a smaller diameter.

These formulae are applied in the particle sizers from Malvern Instrument.

The materials were observed using a confocal microscope sold by Leica under the name True Confocal Scanner Leica TCS SP2.

Example 1

Preparation, Characterizations and Study of a Material in Accordance with the Invention In this example, the preparation, the characterization and the study of a material in accordance with the invention, composed of a silica shell including a crystallizable oil comprising dispersed droplets of aqueous phase, each of said droplets being itself surrounded by a silica shell, are illustrated.

It should be noted that, in this example, the oily and aqueous phases do not include substances of interest, this example being given to demonstrate the structural feasibility of the compartmentalized material according to the process in accordance with the invention.

It is easy to extrapolate the process below to oily and aqueous phases respectively including at least one lipophilic substance of interest and at least one hydrophilic substance of interest. The Rhodamine B used below in the aqueous phase in order to demonstrate the formation of the droplets of aqueous phase surrounded by a silica shell within the oily phase can furthermore be regarded as a hydrophilic substance of interest.

1) Preparation of the Material i): Functionalization of the Silica Particles 5 g of Aerosil® AR 816 silica nanoparticles were dispersed in 100 ml of distilled water using an ultrasonic bath. 9 mg of CTAB/g of particles were subsequently added to this dispersion, this amount representing approximately 1.35 times that of the critical micelle concentration (CMC=0.92 mM). As the surface of the silica nanoparticles is negatively charged, the CTAB (cationic surfactant) is adsorbed at the surface of the silica particles and thus makes it possible to confer on them an amphiphilic nature. An aqueous phase AP1 including a dispersion of silica nanoparticles functionalized at the surface was obtained.

The amount of CTAB was adjusted to the weight of the silica particles in order to obtain a specific coverage of 12 nm$^2$/CTAB molecule at the silica/water interface, all the CTAB used being regarded as adsorbed at the surface of the silica particles.

ii) Preparation of the W/O Emulsion

20% by weight of an aqueous phase AP1 comprising 0.02% by weight of Rhodamine B and 0.1 M of NaCl, preheated to a temperature of 45° C., were introduced into the fatty phase (icosane), also preheated to 45° C. and including a dispersion of AR 972 silica particles. The amount of AR 972 silica particles to be dispersed in the fatty phase is calculated as a function of the amount of aqueous phase, in a proportion of 50 mg of silica particles per gram of aqueous phase.

The emulsification of the fatty phase and of the aqueous phase was carried out using a stirrer sold under the name Ultra-Turrax® T25 by Janke & Kunkel, equipped with an S25 KV-25F dispersing device, ending by stirring at 12 000 revolutions/min for 1 minute. The resulting emulsion was maintained at 45° C. in a thermostatically controlled bath without stirring in order to allow the phenomenon of limited coalescence to occur (adsorption of the silica particles at the surface of the dispersed droplets of aqueous phase, which makes it possible to improve the homogeneity of the distribution in the size of the water droplets dispersed in the oil).

iii) Preparation of the W/O/W Double Emulsion

20% by weight of the W/O emulsion obtained above in the preceding stage were subsequently added to an aqueous phase AP2 comprising 0.1 M of NaCl and the functionalized AR 816 silica particles as prepared above. The amount of functionalized particles depends on the total weight of the W/O emulsion used. In this example, the aqueous phase AP2 included 8 mg of functionalized particles per gram of W/O emulsion introduced into the aqueous phase AP2.

The emulsification of the W/O emulsion in the aqueous phase AP2 was carried out using the same stirrer as above in stage ii), finishing by stirring at 8000 revolutions/min for 2 minutes. The W/O/W double emulsion thus obtained was subsequently kept in a thermostatically controlled bath at 45° C. without stirring for a few minutes in order to allow the phenomenon of limited coalescence to occur (adsorption of the silica particles at the surface of the dispersed droplets of fatty phase).

The emulsion was subsequently removed from the thermostatically controlled bath and then allowed to return to ambient temperature in order to bring about the solidification of the fatty phase.

iv) Mineralization of the Emulsion: Formation of the Silica Shells

The W/O/W double emulsion obtained above in the preceding stage was diluted down to 7% by weight by addition of an aqueous solution comprising 0.5% by weight of CTAB, 46% by weight of 37% by volume hydrochloric acid (HCl) and 0.1 M of NaCl, under cold conditions, that is to say at a temperature of 4° C.

The pH of the mixture thus formed was approximately 0, which subsequently makes it possible to carry out the hydrolysis and the condensation of the TEOS at the oil/water interfaces.

The mineralization of the emulsion was thus carried out by introducing 10 ml of the acidified double emulsion into test tubes and by then adding thereto 0.3 g of TEOS per tube.

The tubes were subjected to continuous stirring on a rotating wheel at the rate of 9 revolutions per minute in a chamber thermostatically controlled at 25° C. After one hour, the expected material was recovered by centrifuging and washed several times with water comprising 0.1 M of NaCl.

The material obtained was stored in pure water for several months. No detrimental change in the capsules was observed during this period.

2) Results and Characterizations

Figure 1:
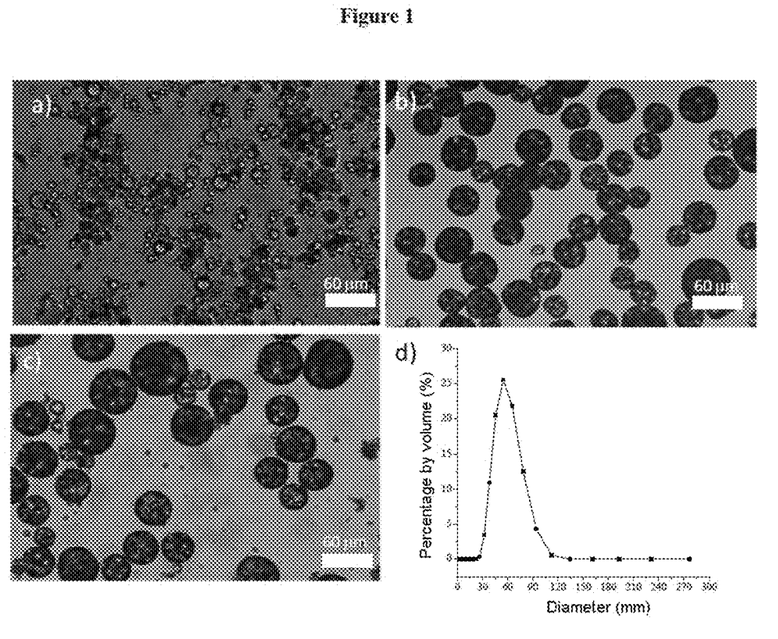
FIGS. 1a-1d are optical microscopy photographs of various emulsions prepared during preparation of the material in accordance with one embodiment.

The appended FIG. 1 represents an optical microscopy photograph of the various emulsions prepared during the preparation of the material in accordance with the invention: FIG. 1a): W/O emulsion; FIG. 1b): W/O/W double emulsion at ambient temperature before the mineralization stage; FIG. 1c): W/O/W double emulsion at ambient temperature after the mineralization stage; FIG. 1d): curve showing the size distribution of the particles of the final material (percentage by volume (%) as a function of the diameter of the particles (mm)).

It was subsequently confirmed that an increase in the temperature brought about rupture of the silica shells and the release of the molten fatty phase and also of the aqueous phase AP1.

Figure 2:
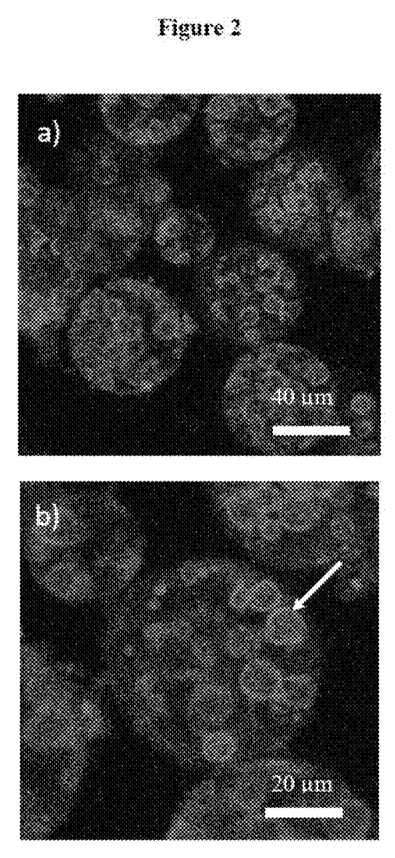
FIGS. 2a-2b are images taken in epifluoroescence confocal microscopy of the material at ambient temperature in accordance with one embodiment.

The appended FIG. 2 is an image taken in epifluorescence confocal microscopy of the material at ambient temperature, that is to say at a temperature at which the fatty phase is in the solid state, and at two different magnifications. In this figure, the white arrow denotes the water/oil interface of the inclusions of droplets of aqueous phase AP1, each encapsulated by a silica shell. The structure of the material in accordance with the invention is clearly seen, by virtue of the Rhodamine B added to the aqueous phase AP1. The Rhodamine B is exclusively present in the droplets of water encapsulated by a silica shell, the concentration of Rhodamine furthermore being higher as the water/oil interface is approached, said encapsulated drops of water being dispersed in the fatty phase, itself encapsulated by a silica shell.

Figure 3:
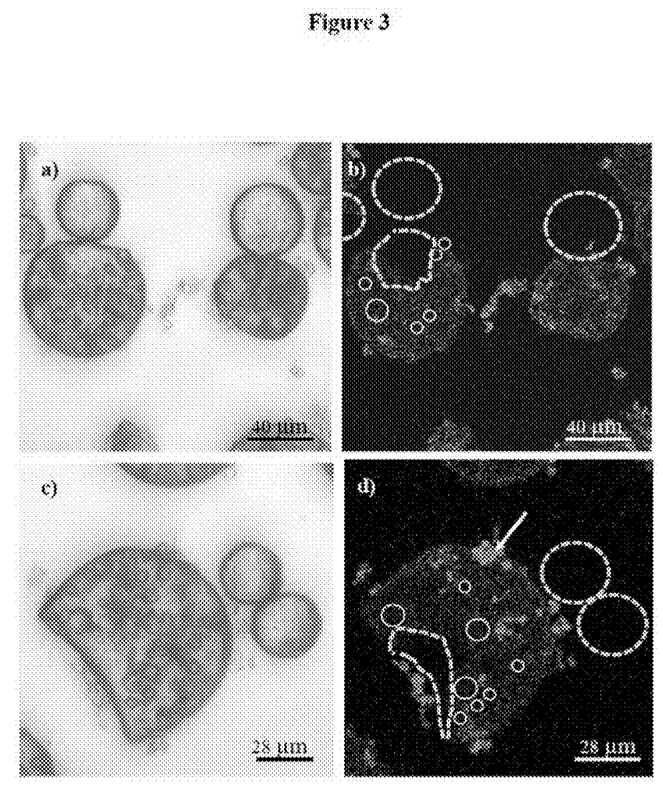
FIGS. 3a-3d are images taken in confocal microscopy of the material at ambient temperature in accordance with one embodiment.

The material was subsequently brought to a temperature of 65° C. by gradually raising the temperature at the rate of 2° C. per minute. The material was subsequently again observed in confocal microscopy after returning to ambient temperature. The corresponding photos are given in the appended FIG. 3, in which FIGS. 3a and 3c are views taken without fluorescence and FIGS. 3b and 3d are views taken with fluorescence, at two different magnifications. In this figure, the thick broken white lines indicate the presence of the fatty phase devoid of fluorescence, the thin broken white lines indicate the impression of the water droplets, these now being devoid of fluorescence, and the white arrow indicates the presence of a few mineralized droplets of water outside the external shell after rupture thereof. It can thus be seen that the heat treatment results in the expulsion of the fatty phase devoid of Rhodamine B by rupture of the silica shell initially surrounding each globule of fatty phase. It is also possible to observe, in FIGS. 3a and 3c, a few droplets without fluorescence corresponding in fact to the impressions left by the water droplets which were initially encapsulated in the internal silica shells and which were scattered after rupture of these internal silica shells. This proves that the TEOS has migrated inside the globules of fatty phase of the W/O/W double emulsion up to the oil/water interface in order to form an internal silica shell around each of the droplets of aqueous phase AP1 which are dispersed in the fatty phase and that the thermal expansion of the fatty phase by raising its temperature brings about both rupture of the external silica shell surrounding the globules of fatty phase and also rupture of the internal silica shells surrounding the droplets of aqueous phase AP1 which are dispersed in the fatty phase.

It is thus possible to simultaneously release lipophilic and hydrophilic substances which would be respectively present in the fatty phase and in the aqueous phase AP1 by simple raising of the temperature of the materials in accordance with the invention.

The invention claimed is:

1. A material in the form of solid particles with a diameter varying from 1 μm to 1 cm which are composed of a continuous shell $E_{Ext}$ comprising:
    at least one silicon oxide, said shell $E_{Ext}$ imprisoning at least one fatty phase, wherein in said material said fatty phase is solid at the storage temperature of said material and comprises from 50% to 99.9% by weight, with respect to the weight of said fatty phase, of a crystallizable oil having a melting point ($T_M$) of less than 100° C. and in that said fatty phase includes at least one lipophilic substance of interest $S_L$ and at least one inclusion comprising a continuous shell $E_{Int}$ comprising at least one silicon oxide, said shell $E_{Int}$ imprisoning an aqueous phase comprising at least one hydrophilic substance of interest $S_H$.

2. The material according to claim 1, wherein the crystallizable oil is chosen from fatty substances and mixtures of fatty substances, of natural or synthetic origin, the melting point of which is greater than 15° C.

3. The material according to claim 1, wherein the crystallizable oil is chosen from paraffin waxes, triglycerides, fatty acids, rosins, waxes, hydrogenated vegetable oils and their mixtures, synthetic bitumens, and their mixtures.

4. The material according to claim 1, wherein the material is provided in the form of a powder of spherical or substantially spherical particles.

5. The material according to claim 1, wherein the silica shell $E_{Ext}$ has a thickness of 0.1 to 2 μm.

6. The material according to claim 1, wherein the silica shell or shells $E_{Int}$ have a thickness varying from 0.1 to 1 μm.

7. The material according to claim 1, wherein the shells $E_{Ext}$ and/or $E_{Int}$ additionally comprise one or more metal oxides of formula $MeO_2$ in which Me is a metal chosen from Zr, Ti, Th, Nb, Ta, V, W and Al.

8. The material according to claim 1, wherein the substance of interest is chosen from medicaments, active principles which can be used in cosmetics, chemical reactants, dyes, pigments and inks.

9. The material according to claim 1, wherein the substance or substances of interest $S_L$ represent from 0.001% to 50% by weight of the total weight of the fatty phase.

10. The material according to claim 1, wherein the substance or substances of interest $S_H$ represent from 0.001% to 50% by weight of the total weight of the aqueous phase present in the inclusion or inclusions present within the fatty phase.

11. A process for the preparation of a material as defined in claim 1, wherein said process comprises the following stages:
    1) in a first stage, bringing a fatty phase comprising from 50% to 99.9% by weight, with respect to the weight of said fatty phase, of a solid crystallizable oil (CO) having a melting point $T_M$ of less than 100° C. to a temperature $T_{CO}$ such that $T_{CO}$ is greater than $T_M$, in order to obtain a crystallizable oil in the liquid state;
    2) in a second stage, incorporating, in the fatty phase in the liquid state, at least one lipophilic substance of interest ($S_L$) and solid colloidal particles P1;
    3) in a third stage, bringing said fatty phase in the liquid state into contact with a first aqueous phase (AP1) brought beforehand to a temperature $T_{AP1}$ such that $T_{AP1}$ is greater than $T_M$, said aqueous phase additionally including at least one hydrophilic substance of interest ($S_H$);
    4) in a fourth stage, subjecting the liquid mixture resulting from the third stage to mechanical stirring in order to obtain a water-in-oil (W/O) emulsion formed of droplets of aqueous phase dispersed in the continuous fatty phase in the liquid state and in which the solid colloidal particles P1 are present at the interface formed between the continuous fatty phase and the dispersed droplets of aqueous phase AP1;
    5) in a fifth stage, adding the W/O emulsion obtained above in the preceding stage to a second aqueous phase (AP2) brought beforehand to a temperature $T_{AP2}$ such that $T_{AP2}$ is greater than $T_M$ and additionally including solid colloidal particles P2, said W/O emulsion representing at most 20% by weight with respect to the weight of the second aqueous phase;
    6) in a sixth stage, subjecting the liquid mixture resulting from the fifth stage to mechanical stirring in order to obtain a water-in-oil-in-water (W/O/W) double emulsion formed of a continuous aqueous phase (AP2) including droplets of fatty phase in the liquid state, each of said droplets of fatty phase in the liquid state including at least one droplet of aqueous phase AP1, in which double emulsion the solid colloidal particles P2 are present at the interface formed between the continuous aqueous phase AP2 and the dispersed droplets of fatty phase in the liquid state;
    7) in a seventh stage, bringing said W/O/W double emulsion to a temperature $T_{W/O/W}$ such that $T_{W/O/W}$ is less than $T_M$ in order to bring about the solidification of the fatty phase and to obtain a W/O/W double emulsion formed of globules of fatty phase in the solid state, each of said globules including at least one droplet of aqueous phase AP1, said globules being dispersed in the aqueous phase AP2;
    8) in an eighth stage, adding, to the aqueous phase AP2 of the double emulsion and with mechanical stirring, at least one silicon oxide precursor and a sufficient amount of at least one acid to bring the aqueous phases AP1 and AP2 to a pH of less than or equal to 4;
    9) in a ninth stage, leaving the W/O/W triple emulsion standing, in order to allow the silicon oxide precursor to hydrolyse and to condense in the form of a silicon oxide shell around said droplets of aqueous phase AP (mineralization of the emulsion) and to thus obtain the expected material; and 10) in a tenth stage, separating said material from the aqueous phase AP2.

12. The process according to claim 11, wherein the solid colloidal particles P1 and P2 are metal oxides chosen from the group consisting of oxides of silicon, titanium, zirconium and iron, and their salts.

13. The process according to claim 11, wherein the solid colloidal particles P1 and P2 are identical in chemical nature and are chosen from silicon oxide nanoparticles.

14. The process according to claim 11, wherein the amount of solid colloidal particles P1 varies from 0.01% to 10% by weight, with respect to the total weight of the aqueous phase AP1.

15. The process according to claim 11, wherein the amount of solid colloidal particles P2 varies from 0.01% to 5% by weight, with respect to the total weight of the W/O emulsion.

16. The process according to claim 11, wherein the solid colloidal particles P1 and P2 are functionalized by adsorption of surfactant molecules at their surface.

17. The process according to claim 11, wherein the silicon oxide precursors are chosen from silicon alkoxides.

18. The process according to claim 17, wherein the silicon alkoxides are chosen from tetramethoxyorthosilane, tetraethoxyorthosilane, dimethyldiethoxysilane, (3-mercaptopropyl)trimethoxysilane, (3-aminopropyl)triethoxysilane, N-(3-trimethoxysilylpropyl)pyrrole, 3-(2,4-dinitrophenylamino)propyltriethoxysilane, N-(2-aminoethyl)-3-aminopropyltrimethoxysilane, phenyltriethoxysilane, methyltriethoxysilane and their mixtures.

19. The process according to claim 11, wherein the amount of silicon oxide precursor varies from 0.005 to 4 $M/m^2$ of surface area of the globules of the dispersed phase of the emulsion and of the droplets of aqueous phase AP1 of the emulsion.

20. A thermostimulated and simultaneous delivery of at least one lipophilic substance of interest and of at least one hydrophilic substance of interest, said delivery comprising the step of:
    delivering said at least one lipohilic substance of interest and of at least one hydrophilic substance of interest via the material of claim 1 in either one of a powder form or a dispersion in a solvent.

21. The thermostimulated and simultaneous delivery of at least one lipophilic substance of interest and of at least one hydrophilic substance of interest according to claim 20, wherein the delivery of the lipophilic and hydrophilic substances of interest is obtained by thermal expansion of the fatty phase, bringing about rupture of the shell surrounding the fatty phase as well as rupture of each of the silica shells surrounding each of the droplets of aqueous phase AP1 dispersed in the fatty phase, under the effect of a rise in the temperature of the material to a delivery temperature $T_D$ such that $T_D > T_M$.

22. A pharmaceutical, cosmetic or food product, comprising:
    as an ingredient, at least one material as defined in claim 1.

* * * * *